US012559706B2

(12) United States Patent
Lu et al.

(10) Patent No.: US 12,559,706 B2
(45) Date of Patent: Feb. 24, 2026

(54) COMPOUND ALGAE CULTURE APPARATUS

(71) Applicant: Hsing-Hong Lu, Hsin Chu (TW)

(72) Inventors: Hsing-Hong Lu, Hsin Chu (TW);
Chao-Hui Lu, Hsin Chu (TW)

(73) Assignee: Hsing-Hong Lu, Hsin Chu (TW)

( * ) Notice: Subject to any disclaimer, the term of this patent is extended or adjusted under 35 U.S.C. 154(b) by 707 days.

(21) Appl. No.: 17/967,866

(22) Filed: Oct. 17, 2022

(65) Prior Publication Data

US 2023/0151315 A1 May 18, 2023

(30) Foreign Application Priority Data

Nov. 18, 2021 (TW) .................................. 110213640

(51) Int. Cl.
  *C12M 1/00* (2006.01)
  *C12M 1/34* (2006.01)
(52) U.S. Cl.
  CPC ............ *C12M 21/02* (2013.01); *C12M 23/58* (2013.01); *C12M 29/10* (2013.01); *C12M 29/22* (2013.01); *C12M 31/10* (2013.01); *C12M 41/12* (2013.01); *C12M 41/30* (2013.01); *C12M 47/02* (2013.01)
(58) Field of Classification Search
  None
  See application file for complete search history.

(56) References Cited

U.S. PATENT DOCUMENTS 7,851,211 B2 12/2010 Lu
8,642,326 B1 2/2014 Schaefer et al.

2007/0289448 A1* 12/2007 Silva ...................... C12M 21/04
                                                              55/467.1
2008/0220514 A1* 9/2008 Lu ........................... C12M 23/06
                                                              435/292.1
2012/0021496 A1* 1/2012 Kim ...................... C12M 21/02
                                                              435/257.1
2017/0137764 A1* 5/2017 Punchard ............... C12M 29/26

FOREIGN PATENT DOCUMENTS

CN       1175279 A   * 3/1998   ............... C12N 1/12
CN     103756886 A   * 4/2014   ............... C12N 1/12
CN     215517424 U     1/2022
JP         49486 A     1/1974
JP       5019982 A     3/1975
WO  WO-2009018498 A2 * 2/2009   ........... G02B 6/4298

* cited by examiner

*Primary Examiner* — Matthew D Krcha
(74) *Attorney, Agent, or Firm* — Li & Cai Intellectual Property Office

(57) ABSTRACT

A compound algae culture apparatus is provided, which includes a photobioreactor module, a growth regulating module, a circulation transfer module, and a circulation pipeline module. The photobioreactor module includes at least one photobioreactor unit, and the growth regulating module includes at least one growth tank unit. The photobioreactor unit includes a light-transmitting coiled pipe. The growth tank unit has a tank body, and a plurality of partitions are disposed in the tank body to divide an inside of the tank body for formation of a curved flow channel A culture fluid for culturing algae passes through the photobioreactor unit and enters the growth tank unit. A volume of the growth tank unit is larger than a volume of the photobioreactor unit, and a residence time of the culture fluid in the growth tank unit is greater than a residence time of the culture fluid in the photobioreactor unit.

9 Claims, 7 Drawing Sheets

COMPOUND ALGAE CULTURE APPARATUS

CROSS-REFERENCE TO RELATED PATENT APPLICATION

This application claims the benefit of priority to Taiwan Patent Application No. 110213640, filed on Nov. 18, 2021. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a compound algae culture apparatus, and more particularly to a compound algae culture apparatus that combines an enclosed photobioreactor and a growth regulating tank and being suitable for usages such as mass culturing.

BACKGROUND OF THE DISCLOSURE

Algae can effectively utilize light energy, carbon dioxide, water and inorganic salts to synthesize proteins, fats, carbohydrates and bioactive substances having high additional values. Due to having high efficiency in converting and utilizing light as nutrients, the algae shows stronger growth potential than advanced plants, such that algae cultivation is generally regarded as having significant importance.

Conventionally, a large-scale industrial production of algae mostly uses an open pond. However, this manner of production takes up too much space, has an unstable yield, and incurs high costs. Moreover, the open pond is easily polluted, light received by the algae is uneven, and a light energy utilization rate is not high. Due to different growth environments, growth conditions of the algae cannot be easily controlled, thereby resulting in death of the algae in a large scale and a low culture efficiency. In order to overcome the shortcomings of the open pond, the industry has developed an enclosed type photobioreactor culturing technology. In this type of culturing technology, the algae is cultivated in an enclosed light-transmitting pipe reactor or an enclosed reactor tank, and light is provided to the enclosed reactor or the enclosed reactor tank through an artificial light source or a natural light source, so that the algae can carry out photosynthesis and grow in an enclosed environment. Such an enclosed type culture apparatus (which utilizes photosynthesis) can save space, but has problems of being expensive and having difficulty in controlling the growth conditions. Further, an enclosed system is prone to problems such as dead algae and blockage. More importantly, the reactor or the reaction tank has a limited capacity, which can result in a low yield, high cultivation costs, difficulty in controlling the quality of the algae, and an inability to cultivate multiple types of algae at the same time.

Based on the above reasons, a conventional algae culture system has certain disadvantages. Therefore, how to redesign the algae culture system through an automatic control of an intelligent system and achieve an improvement via redesigning various factors and structures, so as to overcome the abovementioned deficiencies, has become one of the important issues to be addressed in the relevant industry.

SUMMARY OF THE DISCLOSURE

In response to the above-referenced technical inadequacies, the present disclosure provides a compound algae culture apparatus to overcome problems of a conventional algae culture apparatus. The conventional algae culture apparatus takes up space, is high in costs, and has difficulty in controlling growth conditions, such that the conventional algae culture apparatus is unfit for an industrial production.

In one aspect, the present disclosure provides a compound algae culture apparatus. The compound algae culture apparatus includes a photobioreactor module, a growth regulating module, and an automatic harvesting device. The photobioreactor module includes at least one photobioreactor unit. The at least one photobioreactor unit includes a light-transmitting coiled pipe, and the light-transmitting coiled pipe has a fluid inlet end and a fluid outlet end. The growth regulating module includes at least one growth tank unit. The at least one growth tank unit has a tank body. The tank body has a growth tank inlet and a growth tank outlet, and a plurality of partitions are disposed in the tank body to divide an inside of that tank body for formation of a curved flow channel. A volume of the at least one growth tank unit is configured to be larger than a volume of the at least one photobioreactor unit, and a residence time of a culture fluid in the at least one growth tank unit is not less than a residence time of the culture fluid in the at least one photobioreactor unit. The automatic harvesting device is connected to the growth tank outlet of the at least one growth tank unit. The automatic harvesting device is used for harvesting a portion of algae in the culture fluid. The culture fluid for culturing the algae enters the growth regulating module after carrying out photosynthesis in the photobioreactor module, the culture fluid passes through the automatic harvesting device after passing through the growth regulating module, and the culture fluid re-enters the photobioreactor module after the portion of the algae in the culture fluid is harvested by the automatic harvesting device.

Therefore, in the compound algae culture apparatus provided by the present disclosure, a photobioreactor unit of a pipeline type is combined with a growth tank unit that has a capacity several times greater than a capacity of the photobioreactor unit. Since the photobioreactor unit of a pipeline type has a strong photosynthesis reaction, and the growth tank has a large capacity and allows the growth of the algae to be regulated, a yield and a quality of the algae can be improved.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
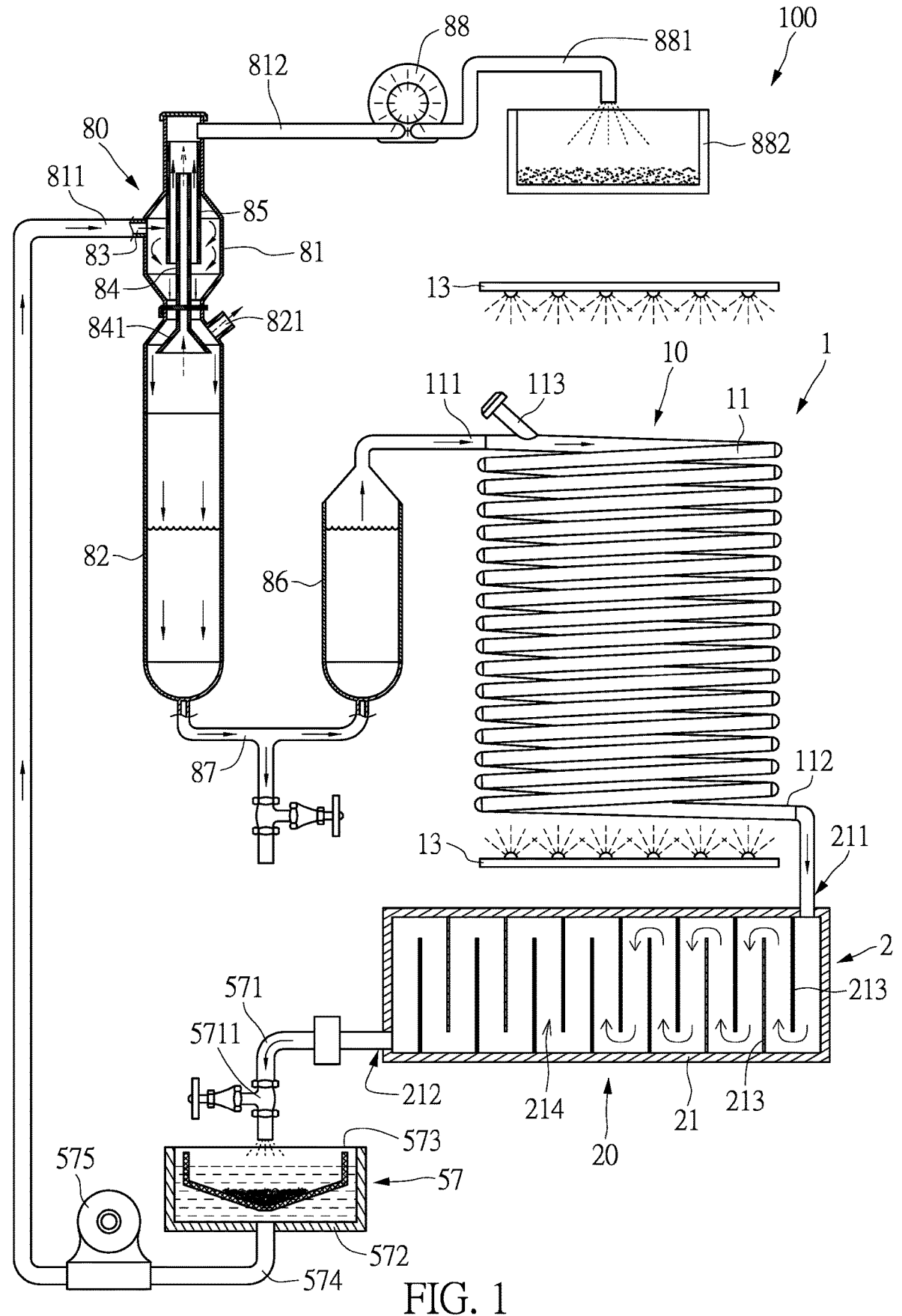
FIG. 1 is a schematic diagram of a compound algae culture apparatus according to a first embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

First Embodiment

Figure 2:
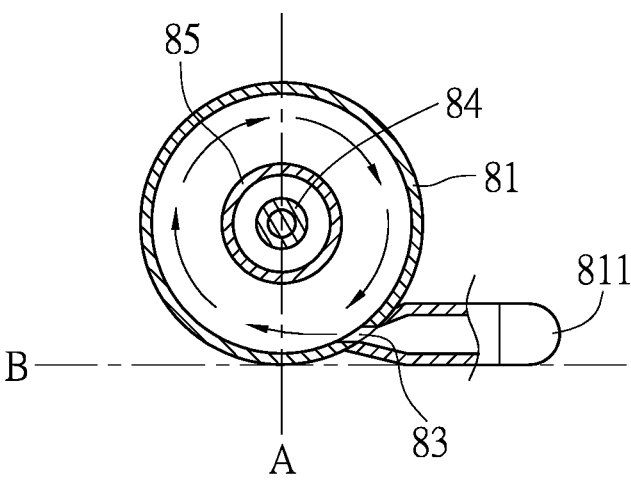
FIG. 2 is a schematic cross-sectional diagram showing configurations of an oxygen discharge cylinder and a fluid inlet port of an oxygen discharge device according to the first embodiment of the present disclosure.

Referring to FIG. 1 and FIG. 2, an embodiment of the present disclosure provides a compound algae culture apparatus. The compound algae culture apparatus includes a photobioreactor module 1, a growth regulating module 2, an automatic harvesting device 57, and an oxygen discharge device 80. The photobioreactor module 1 includes at least one photobioreactor unit 10, and the growth regulating module 2 includes at least one growth tank unit 20. The at least one photobioreactor unit 10 includes a light-transmitting coiled pipe 11, the light-transmitting coiled pipe 11 has a fluid inlet end 111 and a fluid outlet end 112, and the light-transmitting coiled pipe 11 is made of a transparent pipe (e.g., a glass pipe or an acrylic pipe). A culture fluid for culturing algae can enter the light-transmitting coiled pipe 11 from the fluid inlet end 111 and pass through the light-transmitting coiled pipe 11 at a steady flow rate.

A replenishment port 113 can also be disposed on an upper end of the light-transmitting coiled pipe 11, and the replenishment port 113 is provided for an operator to add a new culture fluid or nutrients required for culturing the algae, or to inject carbon dioxide into the light-transmitting coiled pipe 11. The photobioreactor unit 10 can also include multiple fill light devices 13. The fill light devices 13 can be dimmable LED lighting devices, and can generate lights of different wavelengths according to the requirements for cultivating different algae species, so as to improve photosynthesis of the algae.

The at least one growth tank unit 20 is connected to the fluid outlet end 112 of the photobioreactor unit 10, and the growth tank unit 20 has a tank body 21. In this embodiment, the tank body 21 is a rectangular tank body. The tank body 21 of the at least one growth tank unit 20 has a growth tank inlet 211 and a growth tank outlet 212, and a plurality of partitions 213 that are arranged in a staggered manner are disposed in each tank body 21, so that an internal space of the tank body 21 is divided by the plurality of partitions 213 for formation of a curved flow channel 214. In this way, a flow distance of the culture fluid inside the tank body 21 is increased, and a flow time is prolonged.

Particularly, in the present disclosure, a volume of the tank body 21 of the at least one growth tank unit 20 is arranged to be larger than a volume of the at least one photobioreactor unit 10, and a residence time of the culture fluid in the at least one growth tank unit 20 is not less than a residence time of the culture fluid in the at least one photobioreactor unit 10. In one exemplary embodiment of the present disclosure, the volume of the tank body 21 is arranged to be several times larger than the volume of the photobioreactor unit 10, so that an amount of the culture fluid that can be contained in the growth tank unit 20 is several times greater than an amount of the culture fluid that can be contained in the photobioreactor unit 10. Accordingly, a production capacity and a production efficiency can be effectively enhanced.

When the culture fluid enters the tank body 21, the culture fluid can pass through the growth tank unit 20 at a slow flow rate, so that a temperature of the culture fluid can be gradually reduced, and an intensity of the photosynthesis can be reduced or stopped. Therefore, the algae has sufficient time to recover from damages of rapid growth and cell division (which are caused by the photosynthesis), and to digest nutrients obtained in the previous photosynthesis process, such that the algae is grown to a certain size before further division.

The automatic harvesting device 57 is connected to the growth tank outlet 212 of the growth tank unit 20. A harvesting pipe 571 is disposed on the growth tank outlet 212 of the growth tank unit 20, and a harvesting control valve 5711 is disposed on the harvesting pipe 571. The culture fluid discharged from the harvesting pipe 571 can pass through the automatic harvesting device 57, and a portion of the algae in the culture fluid can be harvested through the automatic harvesting device 57. In this embodiment, the automatic harvesting device 57 includes a filter assembly 572 and a culture fluid holding tank 573, and the culture fluid enters the culture fluid holding tank 573 after passing through the filter assembly 572. The filter assembly 572 has pores of appropriate sizes, so that the algae in the culture fluid having a diameter larger than a diameter of the pores of the filter assembly 572 can be blocked by the filter assembly 572.

In particular, the automatic harvesting device 57 of the present disclosure only harvests a certain percentage of the algae in the culture fluid during a harvesting procedure, so that the algae is partially retained in the culture fluid that passes through the automatic harvesting device 57. In addition, a concentration of the algae retained in the culture fluid can be adjusted by controlling the harvesting percentage of the algae, so as to create environmental conditions suitable for the growth of the algae. In this way, the productivity and algae production quality of the compound algae culture apparatus of the present disclosure can be increased.

The automatic harvesting device 57 further includes an outlet pipe 574, which is connected to an outlet of the culture fluid holding tank 573. The outlet pipe 574 is connected to a pressurized transfer device 575, which is a pressurized pump, and an outlet end of the pressurized transfer device 575 is connected to an oxygen discharge cylinder inlet pipe 811 of the oxygen discharge device 80. Through the pressurized transfer device 575, the culture fluid discharged from the automatic harvesting device 57 can be transported into the oxygen discharge device 80, so that excessive oxygen of the culture fluid is discharged from the oxygen discharge device 80 to reduce an oxygen content of the culture fluid.

In this embodiment, the oxygen discharge device 80 includes an oxygen discharge cylinder 81, and a liquid collection cylinder 82 connected to a bottom of the oxygen discharge cylinder 81. The oxygen discharge cylinder 81 is cylindrical-shaped. The oxygen discharge cylinder 81 includes an oxygen discharge pipe 84 arranged at a center of the oxygen discharge cylinder 81, and a hollow pipe 85 sleeved onto an outer side of the oxygen discharge pipe 84. The liquid collection cylinder 82 is connected to the bottom of the oxygen discharge cylinder 81, and a diameter of a junction between the oxygen discharge cylinder 81 and the liquid collection cylinder 82 is decreased to form a connecting neck between the oxygen discharge cylinder 81 and the liquid collection cylinder 82. A lower end of the oxygen discharge pipe 84 passes through the connecting neck and extends into an upper part of the liquid collecting cylinder 82, and an expansion section 841 is formed at the lower end of the oxygen discharge pipe 84.

A diameter of the hollow pipe 85 is larger than that of the oxygen discharge pipe 84, a lower end of the hollow pipe 85 extends to a location near a lower end that is inside the oxygen discharge cylinder 81, and an upper section of the oxygen discharge pipe 84 is fitted into an inside of the hollow pipe 85. An upper end of the hollow pipe 85 extends outside of an upper end of the oxygen discharge cylinder 81, and the upper end of the hollow pipe 85 is connected to a gas extracting device 88 through an air suction pipe 812.

A fluid inlet port 83 is formed on one side of the oxygen discharge cylinder 81, and the fluid inlet port 83 is connected to the oxygen discharge cylinder inlet pipe 811, so that the culture fluid can enter the fluid inlet port 83 through the oxygen discharge cylinder inlet pipe 811 and be delivered into the oxygen discharge cylinder 81 through the fluid inlet port 83. A height of the fluid inlet port 83 is configured to be higher than heights of openings of the lower end of the oxygen discharge pipe 84 and a lower end of the hollow pipe

85, so that the culture fluid sprayed from the fluid inlet port 83 is not suctioned into the hollow pipe 85 and the oxygen discharge pipe 84.

As shown in FIG. 2, in this embodiment, a diameter of the fluid inlet port 83 that is connected to one end of the oxygen discharge cylinder 81 is decreased, so that the fluid inlet port 83 is formed into a nozzle. Further, a central axis of the fluid inlet port 83 is parallel to a tangential direction of a circumferential section of the oxygen discharge cylinder 81, or an included angle of less than 90 degrees is formed therebetween. Therefore, a flow rate of the culture fluid that enters the oxygen discharge cylinder 81 is accelerated, and after the culture fluid contacts an inner wall of the oxygen discharge cylinder 81, the culture fluid can flow in a spiral manner along the inner wall of the oxygen discharge cylinder 81 to the liquid collection cylinder 82 below the oxygen discharge cylinder 81.

When the culture fluid is in a process of flowing from the oxygen discharge cylinder 81 into the liquid collection cylinder 82, gas contained in the culture fluid can be discharged into the oxygen discharge cylinder 81 and the liquid collection cylinder 82, and then be pumped out by the oxygen discharge pipe 84 and the hollow pipe 85. Furthermore, in this process, dead algae in the culture fluid is separated from the culture fluid, extracted by vacuum suction generated by the gas extracting device 88, and discharged into a collection container 882 through a discharge pipe 881. Through the above configuration, an amount of the dead algae in the culture fluid can be decreased, thereby preventing the dead algae from sticking to a flow channel of the overall pipeline or the tank body 21 and causing blockage. Further, algae products produced in this manner do not have an unpleasant odor generated by the dead algae. Instead, the algae products are imbued with the aroma of natural algae, so that the purpose of improving product quality is achieved.

The liquid collection cylinder 82 is connected to the bottom of the oxygen discharge cylinder 81 for accommodating the culture fluid flowing down from the oxygen discharge cylinder 81, and a side exhaust port 821 is disposed on one side of the upper part of the liquid collection cylinder 82. A bottom of the liquid collection cylinder 82 is connected to a bottom of the buffer tank 86 through a connection pipe 87, so that the culture fluid in the liquid collection cylinder 82 flows into the buffer tank 86 through the connecting pipe 87. The buffer tank 86 serves as a buffer space for the culture fluid to enter the photobioreactor unit 10. The culture fluid flown from the oxygen discharge device 80 first enters the buffer tank 86, and then enters the photobioreactor unit 10 from the buffer tank 86, so that the algae in the culture fluid once again carries out the photosynthesis.

Second Embodiment

Referring to FIG. 3 to FIG. 7, a second embodiment of the present disclosure provides a compound algae culture apparatus 100. It should be noted that technical details of this embodiment are similar to those of the first embodiment, and the similarities therebetween will not be reiterated herein.

The compound algae culture apparatus 100 of this embodiment includes: a photobioreactor module 1, a growth regulating module 2, a circulation transfer module 3, a circulation pipeline module 4, a growth monitoring and regulating module 5, and a control module 6.

Figure 4:
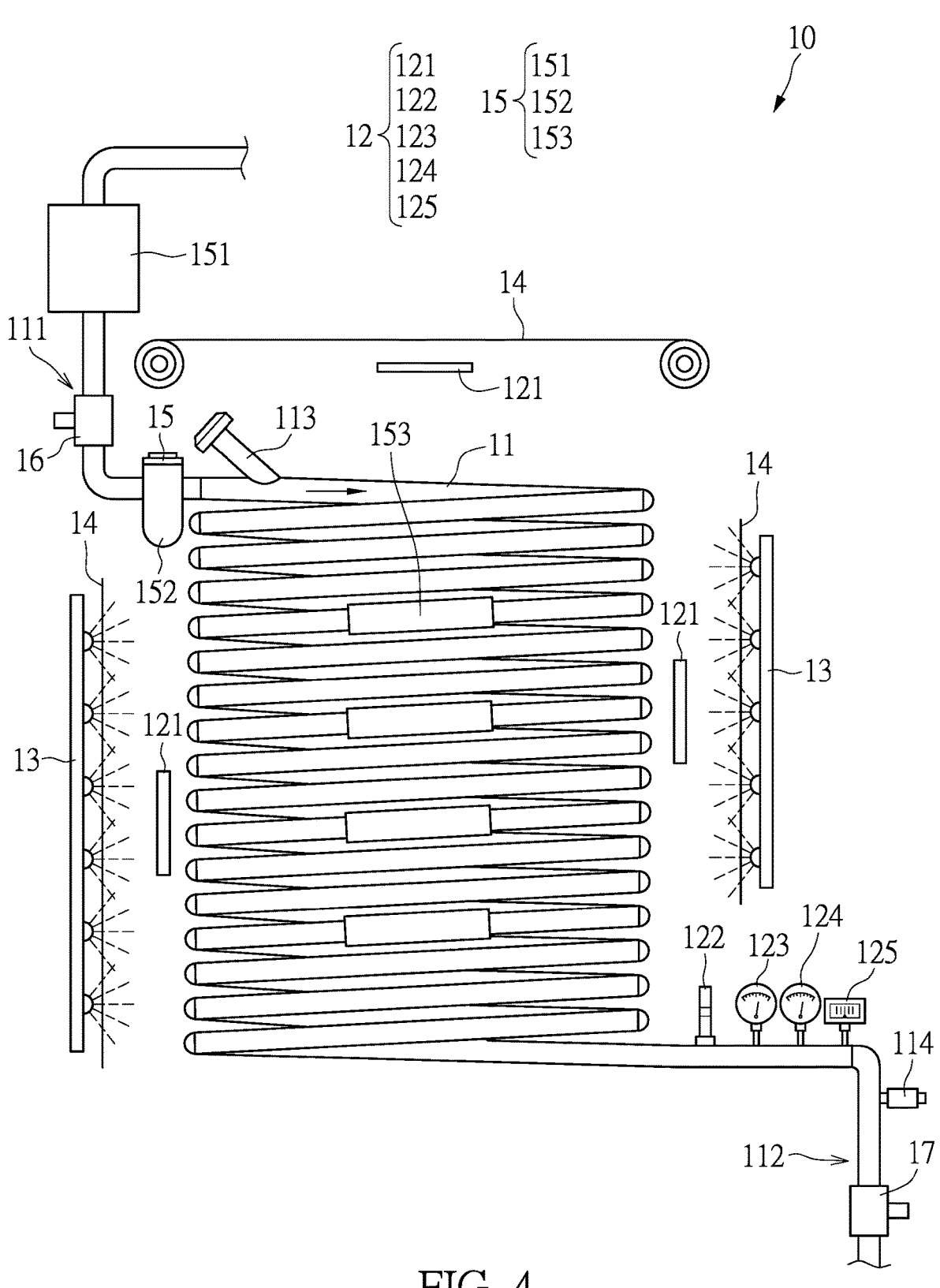
FIG. 4 is a schematic diagram of a photobioreactor unit according to the second embodiment of the present disclosure.

As shown in FIG. 4, the photobioreactor module 1 includes a plurality of photobioreactor units 10. In this embodiment, each of the photobioreactor units 10 includes: a light-transmitting coiled pipe 11, a growth monitoring sub-module 12, a fill light device 13, a shading device 14, a photobioreactor temperature control device 15, a first inlet bypass connector 16, and a first outlet bypass connector 17.

As shown in FIG. 4, the light-transmitting coiled pipe 11 can further have a pressure control valve 114 disposed thereon, so that a pressure of the culture fluid of each of the photobioreactor units 10 can be regulated to be suitable for the growth of the algae. In this embodiment, the growth monitoring sub-module 12 of each of the photobioreactor units 10 includes an illuminance sensor 121, a temperature sensor 122, a pressure sensor 123, a gas concentration sensor 124, and a nutrient concentration sensor 125, so as to monitor growth condition parameters of each of the photobioreactor units 10. The growth condition parameters can include a light intensity, a temperature, a pressure, an oxygen or carbon dioxide concentration, and a nutrient concentration.

As shown in FIG. 4, the shading device 14 of the photobioreactor unit 10 is a sunshade arranged above the light-transmitting coiled pipe 11. An intensity of light that is received by the light-transmitting coiled pipe 11 can be controlled by an opening degree of the shading device 14.

As shown in FIG. 4, in this embodiment, the photobioreactor temperature control device 15 includes: an inlet heat exchanger 151 disposed at the fluid inlet end 111 of the photobioreactor unit 10, an inlet heater 152 disposed at an inlet of the light-transmitting coiled pipe 11, or pipeline heaters 153 disposed at suitable locations of the light-transmitting coiled pipe 11. The photobioreactor temperature control device 15 can be used in cooperation with a water sprinkler and other types of cooling devices to control the temperature of the culture fluid in each of the photobioreactor units 10. The temperature of the culture fluid in each of the photobioreactor units 10 can be adjusted to a temperature suitable for algae growth.

Figure 3:
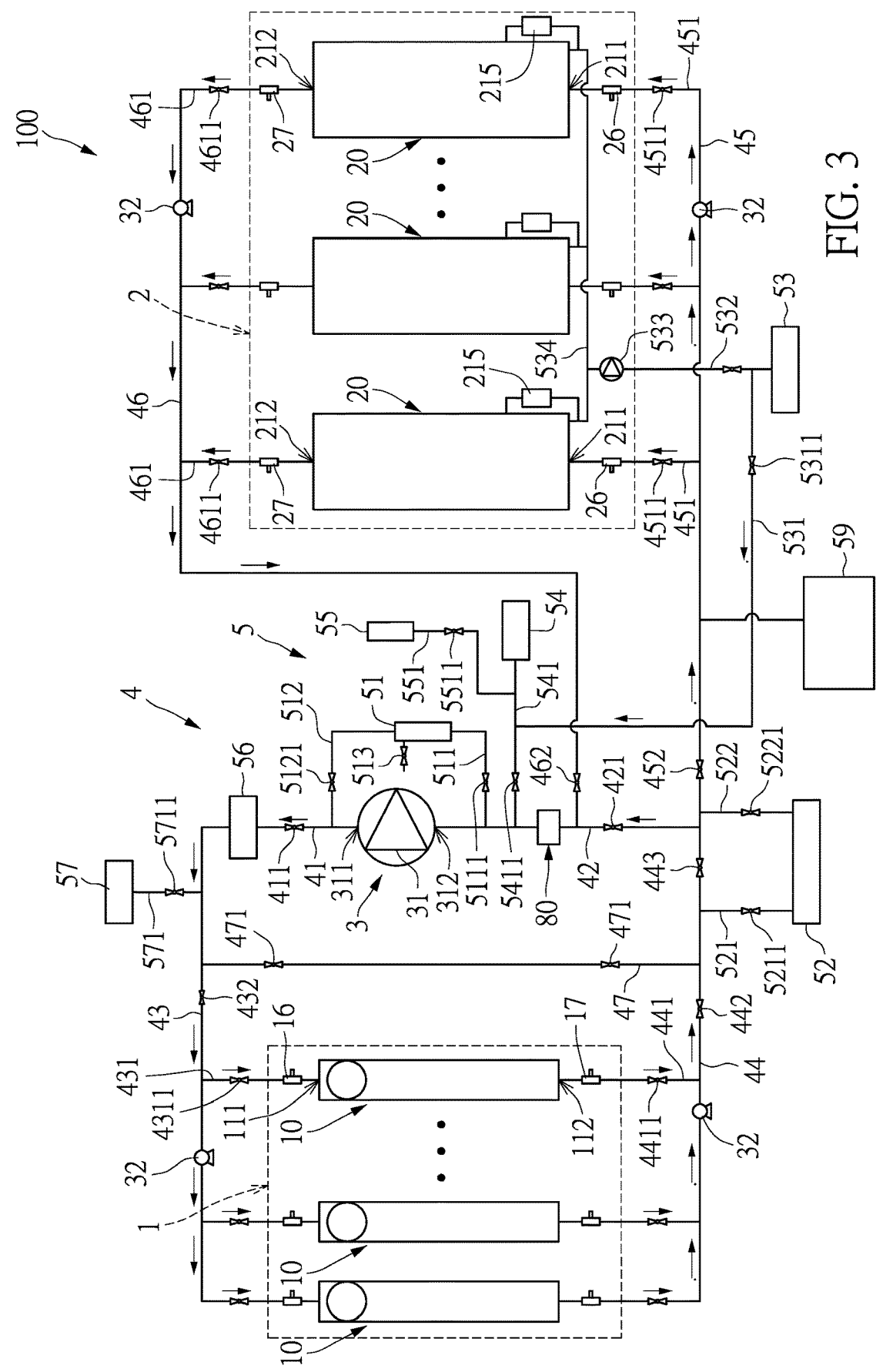
FIG. 3 is a block diagram of a compound algae culture apparatus according to a second embodiment of the present disclosure.

As shown in FIG. 3, the first inlet bypass connector 16 and the first outlet bypass connector 17 of each of the photobioreactor units 10 are disposed at the fluid inlet end 111 and the fluid outlet end 112 of the light-transmitting coiled pipe 11, respectively. Therefore, when one of the photobioreactor units 10 is to be cleaned or used for a mixed culture of another species of algae, the first inlet bypass connector 16 and the first outlet bypass connector 17 can be connected to pipelines of an external circulation device 7 that is used for cleaning pipelines of the photobioreactor units 10 or performing the mixed culture.

Figure 5:
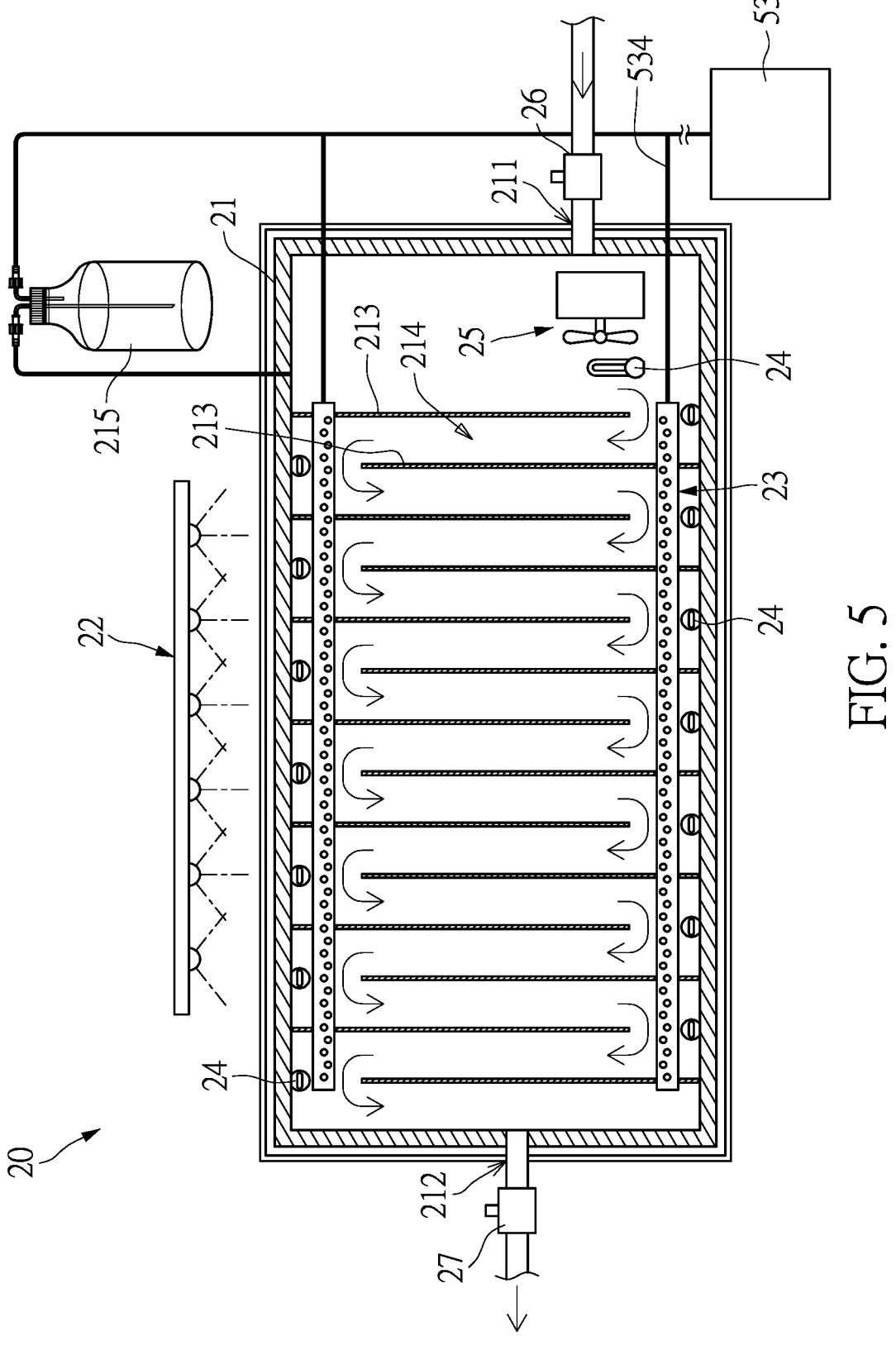
FIG. 5 is a schematic diagram of a growth tank unit according to the second embodiment of the present disclosure.

As shown in FIG. 3 and FIG. 5, in this embodiment, the growth regulating module 2 includes a plurality of growth tank units 20 that correspond to the plurality of photobioreactor units 10. The growth tank units 20 of the growth regulating module 2 are connected to the plurality of photobioreactor units 10 of the photobioreactor module 1 through the circulation pipeline module 4. Furthermore, the culture fluid can be circulated between the plurality of photobioreactor units 10 and the plurality of growth tank units 20 under the control of the circulation transfer module 3 and the circulation pipeline module 4.

As shown in FIG. 5, each of the growth tank units 20 includes a tank body 21, a growth tank light source device 22, a growth tank gas replenishment device 23, a growth tank temperature control device 24, a fluid agitating device 25, a second inlet bypass connector 26, and a second outlet bypass connector 27. The tank body 21 of each of the growth tank units 20 has a growth tank inlet 211 and a growth tank outlet 212, and the culture fluid enters the tank body 21 through the growth tank inlet 211 and exits through the growth tank outlet 212. A plurality of partitions 213 that are arranged in a staggered manner are disposed in the tank body 21, so that an internal space of the tank body 21 is separated by the plurality of partitions 213 to form a curved flow channel 214.

As shown in FIG. 5, the growth tank light source device 22 of each of the growth tank units 20 is disposed above the tank body 21 to regulate a light intensity of light received by the culture fluid in the growth tank unit 20. The growth tank gas replenishment device 23 can be disposed in the tank body 21 and includes a gas conduit, and the growth tank gas replenishment device 23 is connected to a gas pump 533, so that the gas pump 533 fills gas (e.g., carbon dioxide or oxygen) into the growth tank gas replenishment device 23. Then, the gas is injected into the culture fluid in the tank body 21 through air holes of the growth tank gas replenishment device 23. The growth tank temperature control device 24 can be a heater, a heat exchanger, or other temperature control devices disposed in the tank body 21 for regulating the temperature of the culture fluid in the tank body 21. In one exemplary embodiment of the present disclosure, multiple ones of the growth tank temperature control device 24 are disposed at different locations within the tank body 21 for controlling the temperature of the culture fluid at the different locations within the tank body 21. Furthermore, in the tank body 21, the fluid agitating device 25 agitates and drives a water flow to prevent the algae from settling on a tank bottom and resulting in a reduced growth rate. The fluid agitating device 25 can be a motor-driven propeller, or an agitator, a waterwheel, a pump, a wave maker, or other types of devices that can be used to increase a flow rate of the culture fluid or create the water flow. The fluid agitating device 25 is used to form a water flow for which the culture fluid inside the tank body 21 flows from the growth tank inlet 211 of the tank body 21 toward the growth tank outlet 212, thereby allowing the culture fluid inside the tank body 21 to be maintained in a flowing state. Therefore, the algae in the culture fluid can be prevented from precipitating or sticking to an inner side wall of the tank body 21, and a situation in which the culture fluid does not flow sufficiently (which can cause the algae in the culture fluid to be in contact with the growth tank temperature control device 24 for too long such that the algae is overheated and becomes the dead algae, or sticks to the growth tank temperature control device 24) can be avoided.

As shown in FIG. 5, in the present disclosure, the growth tank temperature control devices 24 can be disposed at locations adjacent to a position above the growth tank gas replenishment device 23, so that gas bubbles formed in the culture fluid through the growth tank gas replenishment device 23 can allow the culture fluid around each of the growth tank temperature control devices 24 to flow more completely. Furthermore, in the embodiment shown in FIG. 3, although the fluid agitating device 25 is only shown to be disposed at the growth tank inlet 211 of the tank body 21, the present disclosure is not limited thereto. In other embodiments of the present disclosure not shown in the figures, one fluid agitating device 25 can be disposed in the rear of each of the growth tank temperature control devices 24, such that a better flow agitating effect can be achieved. Therefore, precipitation of the algae in the culture fluid can be avoided, and the situation in which the algae in the culture fluid becomes dead algae due to being in contact with the growth tank temperature control device 24 for too long can also be prevented. Moreover, contact between carbon dioxide and the algae in the culture liquid can be increased, and the algae can receive sufficient illuminance.

As shown in FIG. 5, the second inlet bypass connector 26 and the second outlet bypass connector 27 of each of the growth tank units 20 are connected to the growth tank inlet 211 and the growth tank outlet 212 of the tank body 21, respectively. Therefore, when each of the growth tank units 20 is to be cleaned or temporarily used for a mixed culture of another species of algae (as shown in FIG. 5), the second inlet bypass connector 26 and the second outlet bypass connector 27 can be connected to the pipelines of the external circulation device 7 that is used for cleaning pipelines of the growth tank units 20 or performing the mixed culture.

In addition, as shown in FIG. 3 and FIG. 5, each of the growth tank units 20 can also have a nutrient supply bottle 215 disposed thereon. The nutrient supply bottle 215 is connected to a gas distribution pipe 534, and the nutrient supply bottle 215 can be controlled by air pressure to transport supplemental materials into the growth tank unit 20, or to sample the culture fluid from the growth tank unit 20 for nutrient replenishment, gas addition, sample investigation, etc. When the growth tank unit 20 is used for a mixed culture of different species of algae, each of the growth tank units 20 can have a dedicated nutrient supply bottle 215 for replenishing dedicated nutrition and gas, so as to ensure that the growth tank unit 20 is not contaminated.

In addition, as shown in FIG. 5, the growth regulating module 2 can further include a growth tank feeding device 59 that is simultaneously connected to the plurality of growth tank units 20 through the pipelines. The growth tank feeding device 59 can be used to uniformly replenish supplements (such as gas and nutrients) for each of the growth tank units 20, and can be used to store nutrients or supplements required for cultivating different algae species.

As shown in FIG. 3, the circulation transfer module 3 is connected to the photobioreactor module 1 and the growth regulating module 2 through the circulation pipeline module 4, so that the circulation transfer module 3 can be used to transport the culture fluid. Through the connection of the circulation pipeline module 4, the culture fluid is allowed to flow in the plurality of photobioreactor units 10 of the photobioreactor module 1 and the plurality of growth tank units 20 of the growth regulating module 2.

As shown in FIG. 3, in this embodiment, the circulation transfer module 3 includes a main circulation pump 31 and auxiliary pumps 32 that are scattered and disposed at different locations of the circulation pipeline module 4. The main circulation pump 31 is disposed on a pipeline of the circulation pipeline module 4 between the photobioreactor module 1 and the growth regulating module 2, and is used to pressurize the culture fluid into the pipeline of the circulation pipeline module 4, so as to provide the pressure required for the culture fluid to flow in the circulation pipeline module 4.

As shown in FIG. 3, the circulation pipeline module 4 is used to connect the circulation transfer module 3, the plurality of photobioreactor units 10 of the photobioreactor module 1, and the plurality of growth tank units 20 of the growth regulating module 2. In this embodiment, the circulation pipeline module 4 includes: a main pump outlet pipe 41, a main pump inlet pipe 42, a first inlet main pipe 43, a plurality of first inlet connection pipes 431 connected to the first inlet main pipe 43, a first outlet main pipe 44, a plurality of first outlet connection pipes 441 connected to the first outlet main pipe 44, a second inlet main pipe 45, a plurality of second inlet connection pipes 451 connected to the second inlet main pipe 45, a second outlet main pipe 46, a plurality of second outlet connection pipes 461 connected to the second outlet main pipe 46, and a connection pipeline 47.

As shown in FIG. 3, the main pump outlet pipe 41 is connected to an outlet end 311 of the main circulation pump 31, and the main pump inlet pipe 42 is connected to an inlet end 312 of the main circulation pump 31. Furthermore, the main pump outlet pipe 41 has a main pump inlet control valve 411 disposed thereon, and the main pump inlet pipe 42 has a main pump inlet control valve 421 disposed thereon. The main pump outlet pipe 41 is connected to the first inlet main pipe 43, the first inlet main pipe 43 is connected to the fluid inlet ends 111 of the plurality of photobioreactor units 10 through the plurality of first inlet connection pipes 431, and the first outlet main pipe 44 is connected to the fluid outlet ends 112 of the plurality of photobioreactor units 10 through the plurality of first outlet connection pipes 441, so that the plurality of photobioreactor units 10 are connected in parallel between the first inlet main pipe 43 and the first outlet main pipe 44.

As shown in FIG. 3, an outlet end of the first outlet main pipe 44 is connected to an inlet end of the main pump inlet pipe 42 and an inlet end of the second inlet main pipe 45. The second inlet main pipe 45 is connected to the growth tank inlets 211 of the plurality of growth tank units 20 through the plurality of second inlet connection pipes 451, and the second outlet main pipe 46 is connected to the growth tank outlets 212 of the plurality of growth tank units 20 through the plurality of second outlet connection pipes 461. Therefore, the plurality of growth tank units 20 are connected in parallel between the second inlet main pipe 45 and the second outlet main pipe 46. One end of the second outlet main pipe 46 away from the plurality of growth tank units 20 is connected to the main pump inlet pipe 42 at a location between the main pump inlet control valve 421 and the inlet end 312 of the main circulation pump 31.

As shown in FIG. 3, each of the first inlet connection pipes 431 has a first inlet control valve 4311 disposed thereon, and each of the first outlet connection pipes 441 has a first outlet control valve 4411 disposed thereon. Furthermore, each of the second inlet connection pipes 451 has a second inlet control valve 4511 disposed thereon, and each second outlet connection 461 has a second outlet control valve 4611 disposed thereon. When the first inlet control valve 4311 and the first outlet control valve 4411 corresponding to any one of the photobioreactor units 10 are closed, the culture fluid cannot pass through the photobioreactor unit 10, such that the photobioreactor unit 10 is in a closed state. Similarly, when the second outlet control valve 4611 and the second inlet control valve 4511 corresponding to any one of the growth tank units 20 are closed, the culture fluid cannot pass through the growth tank unit 20, such that the growth tank unit 20 is in a closed state.

As shown in FIG. 3, the first inlet control valve 4311 of each of the photobioreactor units 10 is disposed on a location of the first inlet connection pipe 431 (that corresponds to each of the photobioreactor units 10) between the first inlet bypass connector 16 and the first inlet main pipe 43, and the first outlet control valve 4411 of each of the photobioreactor units 10 is disposed on a location of the first outlet connection pipe 441 (that corresponds to each of the photobioreactor units 10) between the first outlet bypass connector 17 and the first outlet main pipe 44. Similarly, the second inlet control valve 4511 of each of the growth tank units 20 is disposed on a location of the second inlet connection 451 (that corresponds to each of the growth tank units 20) between the second inlet bypass connector 26 and the second inlet main pipe 45, and the second outlet control valve 4611 of each of the growth tank units 20 is disposed on a location of the second outlet connection 461 (that corresponds to each of the growth tank units 20) between the second outlet bypass connector 27 and the second outlet main pipe 46.

Figure 7:
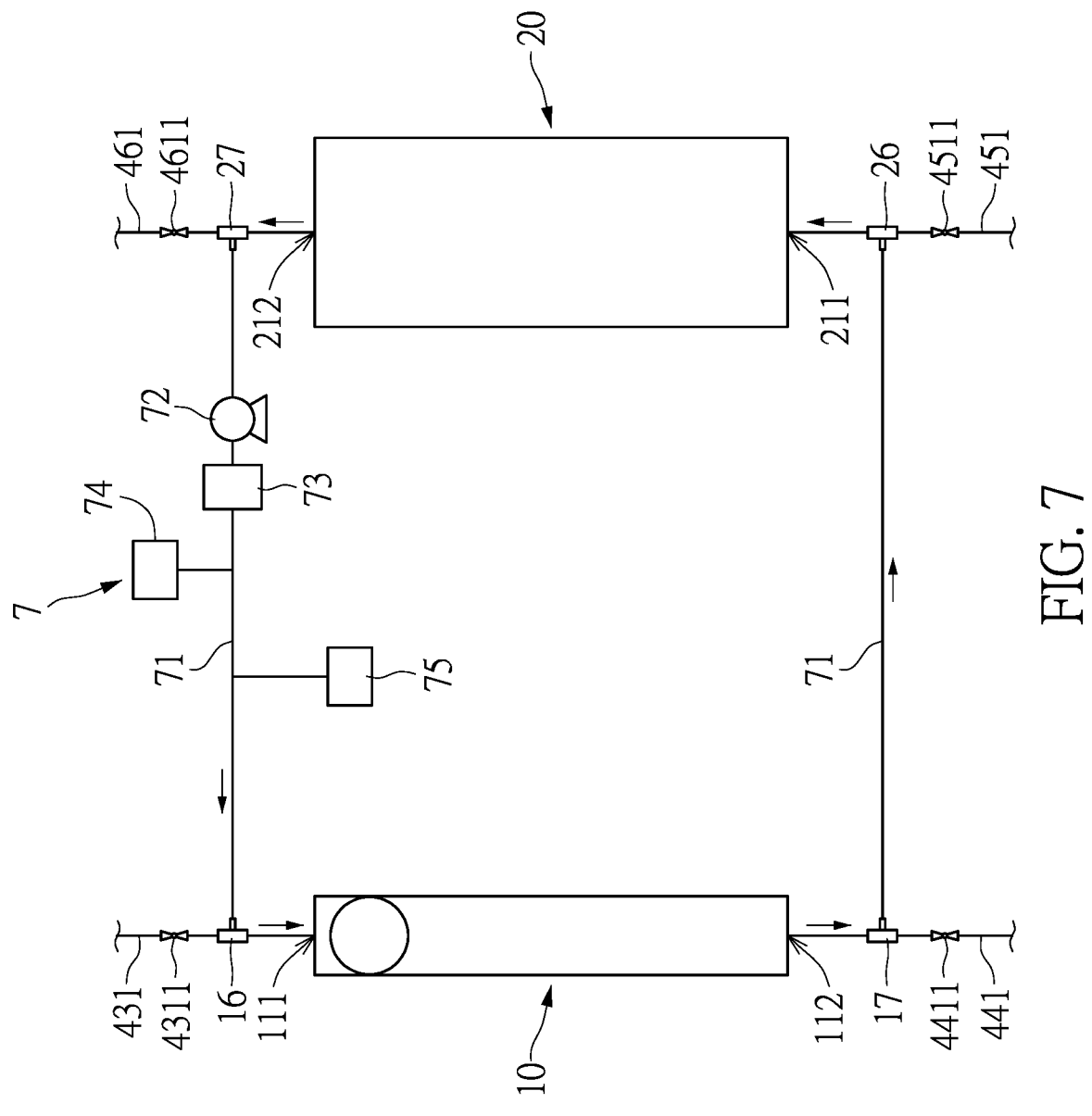
FIG. 7 is a schematic diagram showing the photobioreactor unit and the growth tank unit in the compound algae culture apparatus of the present disclosure being connected to an external circulation device for a mixed culture of algae.

Therefore, as shown in FIG. 7, when any of the photobioreactor unit 10 or the growth tank unit 20 is to be cleaned or used for a mixed culture of different species of algae, the first inlet control valve 4311 and the first outlet control valve 4411 of the photobioreactor unit 10 can be closed, and the second inlet control valve 4511 and the second outlet control valve 4611 of the growth tank unit 20 can closed, so as to prevent cleaning water or the culture fluid for the mixed culture of other species of algae from entering into the circulation pipeline module 4 and causing contamination of the culture fluid in the circulation pipeline module 4 and other components of the compound algae culture apparatus.

As shown in FIG. 3, the circulation pipeline module 4 can further control a circulation path of the culture fluid through the connection pipeline 47 and a plurality of flow control valves. The connection pipeline 47 is connected to one end of the first inlet main pipe 43 and one end of the first outlet main pipe 44 that are adjacent to the main circulation pump 31, and two connection pipeline control valves 471 are disposed at two ends of the connection pipeline 47, respectively. Furthermore, a first flow control valve 432 is disposed on a location of the first inlet main pipe 43 between the connection pipeline 47 and one of the first inlet connection pipes 431 that is most adjacent to the main circulation pump 31. A second flow control valve 442 is disposed on a location of the first outlet main pipe 44 between the connection pipeline 47 and one of the first outlet connection pipes 441 that is most adjacent to the main circulation pump 31. A third flow control valve 443 is disposed on a location of the first outlet main pipe 44 between the connection pipeline 47 and the main pump inlet pipe 42. A fourth flow control valve 452 is disposed on a location of the second inlet main pipe 45 between the main pump inlet pipe 42 and one of the second inlet connection pipes 451 that is most adjacent to the main circulation pump 31. A fifth flow control valve 462 is disposed on a location of the second outlet main pipe 46 between the main pump inlet pipe 42 and one of the second outlet connection pipes 461 that is most adjacent to the main circulation pump 31.

As shown in FIG. 3, through the growth monitoring and regulating module 5, the compound algae culture apparatus 100 can monitor the culture of the algae, control growth conditions of the algae, replenish the gas, nutrients, or algae seedlings required for algae growth according to requirements, monitor a growth status of the algae, and timely harvest the algae. In this embodiment, the growth monitoring and regulating module 5 includes: a monitoring module 51, a main circulation temperature control device 52, a feeding device 54, a gas replenishment device 53, an algae replenishment device 55, an algae growth monitoring device 56, the automatic harvesting device 57, and the oxygen discharge device 80.

As shown in FIG. 3, the monitoring module 51 is a sensor module that includes various types of sensors (e.g., a temperature sensor, a pressure sensor, a nutrient concentration sensor, a pH sensor, a carbon dioxide concentration sensor, and an oxygen concentration sensor). The monitoring module 51 is used to monitor a water temperature, a pH value, a content of dissolved oxygen, a nutrient concentration, a turbidity, a carbon dioxide concentration, an oxygen concentration, and other parameters of the culture fluid for algae cultivation. In this embodiment, the monitoring module 51 is connected to the main pump inlet pipe 42 and the main pump outlet pipe 41 through bypass pipes 511 and 512, and bypass control valves 5111 and 5121 are respectively disposed on the bypass pipes 511 and 512 to control a flow amount of the culture fluid that passes through the monitoring module 51 via the bypass pipes 511 and 512. In addition, the monitoring module 51 is connected to a drain valve 513 for sampling the culture fluid for inspection and analysis.

As shown in FIG. 3, the main circulation temperature control device 52 can be a heat exchanger, a heater, or a cooler. In this embodiment, the main circulation temperature control device 52 is connected between the first outlet main pipe 44 and the second inlet main pipe 45 via bypass pipes 521 and 522, and bypass control valves 5211 and 5221 are disposed on the bypass pipes 521 and 522, respectively. Furthermore, in this embodiment, the third flow control valve 443 is disposed between the bypass pipe 521 and the bypass pipe 522. As such, when the third flow control valve 443 is closed and the bypass control valves 5211 and 5222 are opened, the culture fluid can flow through the main circulation temperature control device 52, so that the temperature of the culture fluid can be adjusted.

As shown in FIG. 3, the feeding device 54 is connected to the main pump inlet pipe 42 through a supply pipe 541, and the supply pipe 541 has a supply control valve 5411 disposed thereon. The feeding device 54 can be used to replenish the nutrients in the culture fluid, add chemicals to adjust the pH value of the culture fluid, or replenish nutrients required for the growth of other species of algae. The gas replenishment device 53 is connected to the main pump inlet pipe 42 through a gas replenishment pipe 531, and the gas replenishment pipe 531 has a gas control valve 5311 disposed thereon. In this embodiment, the gas replenishment device 53 also includes a second gas replenishment pipe 532, and the second gas replenishment pipe 532 is connected to a gas pump 533. Through the gas distribution pipe 534, the gas pump 533 is further connected to the growth tank gas replenishment devices 23 of the growth tank units 20 of the growth regulating module 2. The gas replenishment device 53 can be used to provide carbon dioxide or oxygen, so that the carbon dioxide or oxygen can be replenished when the carbon dioxide or oxygen concentration in the culture fluid is insufficient.

As shown in FIG. 3, the algae replenishment device 55 is connected to the supply pipe 541 through an algae supply pipe 551, and an algae supply control valve 5511 is disposed on the algae supply pipe 551 for controlling the algae supply pipe 551 to be opened or closed. The algae replenishment device 55 is used to replenish the algae seedlings or the algae that is cultivated into the culture fluid, so as to adjust a density of the algae in the culture fluid. The algae growth monitoring device 56 is disposed between the main pump outlet pipe 41 and the first inlet main pipe 43. The algae growth monitoring device 56 can monitor the growth status of the algae (which includes information such as the density of the algae, a color of the algae, and a growth size of the algae) in the culture fluid through optical means. The automatic harvesting device 57 is connected between the main pump outlet pipe 41 and the first inlet main pipe 43 through the harvesting pipe 571. The automatic harvesting device 57 can work in conjunction with the algae growth monitoring device 56. When the algae growth monitoring device 56 detects that the density and the growth size of the algae in the culture fluid meet harvesting conditions, the automatic harvesting device 57 can begin harvesting the algae.

As shown in FIG. 3, in this embodiment, the oxygen discharge device 80 is disposed on the main pump inlet pipe 42. After the culture fluid passes through the photobioreactor module 1 and the growth regulating module 2 but before the culture fluid is recirculated to the inlet end 312 of the main circulation pump 31, the culture fluid can first enter the oxygen discharge device 80, so that the excessive oxygen and the dead algae in the culture fluid are removed.

Figure 6:
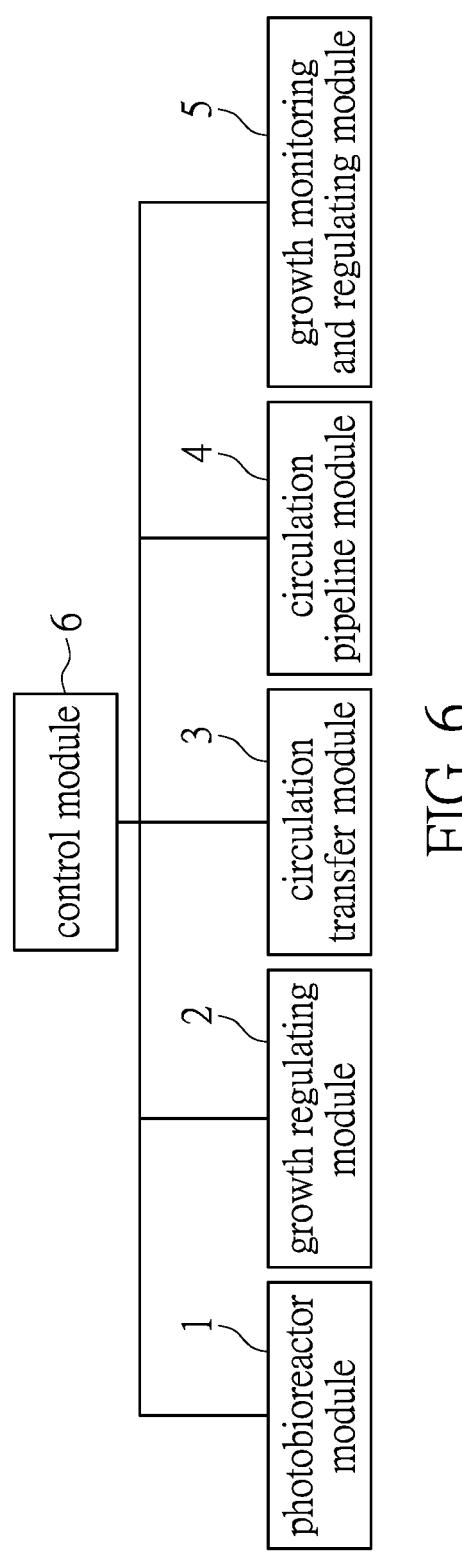
FIG. 6 is a block diagram showing a connection relationship of a control module and each component in the compound algae culture apparatus according to the present disclosure.

As shown in FIG. 6, the compound algae culture apparatus 100 of the present disclosure further includes the control module 6. In this embodiment, the control module 6 is coupled to the photobioreactor module 1, the growth regulating module 2, the circulation transfer module 3, the circulation pipeline module 4, and the growth monitoring and regulating module 5. The control module 6 can be a central control computer or an information device capable of remote control, and remote controlling in the present disclosure can also be achieved by using the Internet and applications on a smartphone. The control module 6 can be used to receive parameters or monitoring data detected by the aforementioned sensors, and to control the various control valves of the circulation pipeline module 4 and various sub-modules or devices of the monitoring module 51. In this way, an operation of the compound algae culture apparatus 100 can be controlled, thereby achieving purposes of monitoring the growth conditions of the algae, automatically replenishing or adjusting parameters of the growth conditions of the algae, and automatically harvesting the algae.

Reference is made to FIG. 7, which shows a use mode in which the compound algae culture apparatus 100 of the present disclosure uses some of the photobioreactor units 10 and the growth tank units 20 for a mixed culture. In this embodiment, the first inlet control valve 4311 and the first outlet control valve 4411 corresponding to one of the photobioreactor units 10 are closed, and the second inlet control valve 4511 and the second outlet control valve 4611 corresponding to one of the growth tank units 20 are closed. Then, the external circulation device 7 is connected between the first inlet bypass connector 16 and the first outlet bypass connector 17 of the photobioreactor units 10 and the second inlet bypass connector 26 and the second outlet bypass connector 27 of the growth tank unit 20, which allows the culture fluid to circulate and flow between the photobioreactor unit 10 and the growth tank unit 20 without flowing into the circulation pipeline module 4 (so as to prevent contamination of the culture fluid of the compound algae culture apparatus 100).

In more detail, the external circulation device 7 includes: a plurality of external hoses 71, an external circulation pump 72, an external temperature control device 73, an external gas replenishment device 74, and an external feeding device 75. The plurality of external hoses 71 are connected between the first outlet bypass connector 17 of the photobioreactor unit 10 and the second inlet bypass connector 26 of the growth tank unit 20, and between the second outlet bypass connector 27 and the first inlet bypass connector 16. The external circulation pump 72, the external temperature control device 73, the external gas replenishment device 74, and the external feeding device 75 are all connected to the plurality of external hoses 71, so that the culture fluid can be circulated between the photobioreactor unit 10 and the growth tank unit 20 through the external circulation pump 72.

BENEFICIAL EFFECTS OF THE EMBODIMENTS

One of the beneficial effects of the present disclosure is that, by virtue of "a photobioreactor unit of a pipeline type being combined with a growth tank unit that has a capacity several times greater than a capacity of the photobioreactor unit," the photobioreactor unit of a pipeline type has a strong photosynthesis reaction, and the growth tank has a large capacity and allows the growth of the algae to be regulated, thereby a yield and a quality of the algae can be improved.

Another beneficial effect of the present disclosure is that, the compound algae culture apparatus of the present disclosure can be connected to the photobioreactor module, the growth regulating module, and the circulation transfer module through the circulation pipeline module. Hence, the compound algae culture apparatus of the present disclosure meets the requirements of an industrial mass production due to having the flexibility of easily increasing the production capacity. In addition, a set of main circulation pumps can work in cooperation with the circulation pipeline module to circulate the culture fluid between different photobioreactor units and different growth tank units. In this way, centralized control can be achieved, the structure can be simplified, and production costs can be reduced.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A compound algae culture apparatus, comprising:
a photobioreactor module including at least one photobioreactor unit, wherein the at least one photobioreactor unit includes a light-transmitting coiled pipe, and the light-transmitting coiled pipe has a fluid inlet end and a fluid outlet end;
a growth regulating module including at least one growth tank unit, wherein the at least one growth tank unit has a tank body, the tank body has a growth tank inlet and a growth tank outlet, and a plurality of partitions are disposed in the tank body to divide an inside of the tank body for formation of a curved flow channel; wherein a volume of the at least one growth tank unit is configured to be larger than a volume of the at least one photobioreactor unit, and a residence time of a culture fluid in the at least one growth tank unit is not less than a residence time of the culture fluid in the at least one photobioreactor unit; and
an automatic harvesting device connected to the growth tank outlet of the at least one growth tank unit, wherein the automatic harvesting device is used for harvesting a portion of algae in the culture fluid;
wherein the culture fluid for culturing the algae enters the growth regulating module after carrying out photosynthesis in the photobioreactor module, the culture fluid passes through the automatic harvesting device after passing through the growth regulating module, and the culture fluid re-enters the photobioreactor module after the portion of the algae in the culture fluid is harvested by the automatic harvesting device;
wherein the at least one growth tank unit further includes a growth tank light source device, a growth tank gas replenishment device, a plurality of growth tank temperature control devices, and a fluid agitating device; wherein the growth tank light source device is disposed above the at least one growth tank unit, the growth tank gas replenishment device is disposed in the at least one growth tank unit for injecting gas into the culture fluid in the at least one growth tank unit, the growth tank temperature control devices are disposed in the at least one growth tank unit for controlling a temperature of the culture fluid in the at least one growth tank unit, and the fluid agitating device is disposed in the at least one growth tank unit for agitating a water flow.

2. The compound algae culture apparatus according to claim 1, wherein the photobioreactor module includes multiple ones of the photobioreactor unit, and the growth regulating module includes multiple ones of the growth tank unit; wherein the compound algae culture apparatus further comprises:

a circulation transfer module having a main circulation pump, wherein the main circulation pump has an inlet end and an outlet end; and a circulation pipeline module including:

a main pump outlet pipe connected to the outlet end of the main circulation pump;

a main pump inlet pipe connected to the inlet end of the main circulation pump;

a first inlet main pipe connected to a plurality of first inlet connection pipes, wherein the first inlet connection pipes are respectively connected between the fluid inlet ends of the photobioreactor units and the first inlet main pipe, and each of the first inlet connection pipes has a first inlet control valve disposed thereon;

a first outlet main pipe connected to a plurality of first outlet connection pipes, wherein the first outlet connection pipes are respectively connected between the fluid outlet ends of the photobioreactor units and the first outlet main pipe, and each of the first outlet connection pipes has a first outlet control valve disposed thereon;

a second inlet main pipe connected to a plurality of second inlet connection pipes, wherein the second inlet connection pipes are respectively connected between the growth tank inlets of the growth tank units and the second inlet main pipe, and each of the second inlet connection pipes has a second inlet control valve disposed thereon; and a second outlet main pipe connected to a plurality of second outlet connection pipes, wherein the second outlet connection pipes are respectively connected between the growth tank outlets of the growth tank units and the second outlet main pipe, and each of the second outlet connection pipes has a second outlet control valve disposed thereon;

wherein the photobioreactor units are connected in parallel between the first inlet main pipe and the first outlet main pipe via the first inlet connection pipes and the first outlet connection pipes, and the growth tank units are connected in parallel between the second inlet main pipe and the second outlet main pipe via the second inlet connection pipes and the second outlet connection pipes;

wherein the main pump outlet pipe is connected to the first inlet main pipe, one end of the first outlet main pipe is connected to the second inlet main pipe, and one end of the second outlet main pipe is connected to the main pump inlet pipe, such that the culture fluid pumped out from the main circulation pump enters the photobioreactor units through the first inlet main pipe, flows from the first outlet main pipe to the second inlet main pipe to pass through the growth tank units, and enters the second outlet main pipe before flowing to the main pump inlet pipe.

3. The compound algae culture apparatus according to claim 2, wherein one end of the main pump inlet pipe opposite to the main circulation pump is connected to the first outlet main pipe and the second inlet main pipe, and the main pump inlet pipe has a main pump inlet control valve disposed thereon; wherein the circulation pipeline module further includes:

a connection pipeline, wherein the connection pipeline is connected to one end of the first inlet main pipe and one end of the first outlet main pipe that are adjacent to the main circulation pump, and the connection pipeline has at least one connection pipeline control valve disposed thereon;

a first flow control valve disposed on a location of the first inlet main pipe between the connection pipeline and one of the first inlet connection pipes that is most adjacent to the main circulation pump;

a second flow control valve disposed on a location of the first outlet main pipe between the connection pipeline and one of the first outlet connection pipes that is most adjacent to the main circulation pump;

a third flow control valve disposed on a location of the first outlet main pipe between the connection pipeline and the main pump inlet pipe;

a fourth flow control valve disposed on a location of the second inlet main pipe between the main pump inlet pipe and one of the second inlet connection pipes that is most adjacent to the main circulation pump; and a fifth flow control valve disposed on a location of the second outlet main pipe between the main pump inlet pipe and one of the second outlet connection pipes that is most adjacent to the main circulation pump.

4. The compound algae culture apparatus according to claim 3, further comprising:

an oxygen discharge device disposed at an inlet of the photobioreactor module, wherein the oxygen discharge device includes an oxygen discharge cylinder and a liquid collection cylinder connected to a bottom of the oxygen discharge cylinder; wherein the oxygen discharge cylinder includes an oxygen discharge pipe arranged at a center of the oxygen discharge cylinder and a hollow pipe sleeved onto an outer side of the oxygen discharge pipe; wherein an upper end of the hollow pipe extends outside of an upper end of the oxygen discharge cylinder, an upper section of the oxygen discharge pipe is fitted into an inside of the hollow pipe, and a gap is maintained between the hollow pipe and the oxygen discharge pipe;

a fluid inlet port formed on one side of the oxygen discharge cylinder, wherein the fluid inlet port is connected to a pressurized transfer device, the culture fluid is sprayed inside the oxygen discharge cylinder through the fluid inlet port and then flows into the liquid collection cylinder, and oxygen contained in the culture fluid is discharged outside the oxygen discharge cylinder through the oxygen discharge pipe and the hollow pipe; and a gas extracting device, wherein the gas extracting device is connected to an outlet of the oxygen discharge pipe for generating a vacuum suction, so as to extract the oxygen discharged from the oxygen discharge pipe and dead algae in the culture fluid from the oxygen discharge device;

wherein the culture fluid passes through the photobioreactor units, the growth tank units, and the oxygen discharge device, and then re-enters the photobioreactor units for carrying out the photosynthesis.

5. The compound algae culture apparatus according to claim 4, wherein a lower end of the oxygen discharge pipe extends to an upper end of the liquid collection cylinder, and wherein a height of the fluid inlet port is configured to be higher than heights of openings of the lower end of the oxygen discharge pipe and a lower end of the hollow pipe.

6. The compound algae culture apparatus according to claim 5, further comprising a growth monitoring and regulating module, wherein the growth monitoring and regulating module includes:

a monitoring module connected to the main pump inlet pipe and the main pump outlet pipe, wherein the monitoring module includes a plurality of sensors for monitoring a water temperature, a pH value, a content of dissolved oxygen, a nutrient concentration, a turbidity, a carbon dioxide concentration, and an oxygen concentration of the culture fluid;

a main circulation temperature control device connected between the first outlet main pipe and the second inlet main pipe to control a temperature of the culture fluid;

a feeding device;

a gas replenishment device; and an algae replenishment device;

wherein the feeding device, the gas replenishment device, and the algae replenishment device are connected to the main pump inlet pipe for replenishing the culture fluid with nutrients, carbon dioxide or oxygen, and the algae.

7. The compound algae culture apparatus according to claim 6, wherein the growth monitoring and regulating module further includes an algae growth monitoring device, and the algae growth monitoring device is connected between the main pump outlet pipe and the first inlet main pipe for monitoring a growth status of the algae in the culture fluid and controlling the automatic harvesting device to harvest the algae in the culture fluid when the algae in the culture fluid grows to meet harvesting conditions.

8. The compound algae culture apparatus according to claim 2, wherein each of the photobioreactor units has a first inlet bypass connector disposed at the fluid inlet end and a first outlet bypass connector disposed at the fluid outlet end, and each of the growth tank units has a second inlet bypass connector disposed at the growth tank inlet and a second outlet bypass connector disposed at the growth tank outlet.

9. The compound algae culture apparatus according to claim 1, wherein the at least one photobioreactor unit further includes a growth monitoring sub-module, a fill light device, a shading device, and a photobioreactor temperature control device; wherein the growth monitoring sub-module includes a plurality of illuminance sensors, and a temperature sensor, a pressure sensor, a gas concentration sensor, and a nutrient concentration sensor disposed on the light-transmitting coiled pipe; wherein the fill light device is an LED device.

* * * * *